United States Patent [19]

Kusuda et al.

[11] Patent Number: 5,545,751
[45] Date of Patent: Aug. 13, 1996

[54] PROCESS FOR THE PREPARATION OF 4-METHOXY-2,2',6'-TRIMETHYLDIPHENYLAMINE

[75] Inventors: Chiyuki Kusuda, Kumamoto-ken; Masayuki Furuya, Fukuoka-ken; Masaru Wada, Fukuoka-ken; Yoshihiro Irizato, Fukuoka-ken; Hiroshi Naruse, Fukuoka-ken; Teruyuki Nagata, Fukuoka-ken, all of Japan

[73] Assignee: Mitsui Toatsu Chemicals, Inc., Tokyo, Japan

[21] Appl. No.: 358,566

[22] Filed: Dec. 14, 1994

[30] Foreign Application Priority Data

Dec. 27, 1993 [JP] Japan ..................................... 5-331981

[51] Int. Cl.$^6$ .................................................. C07C 209/22
[52] U.S. Cl. ........................... 564/398; 564/397; 564/433
[58] Field of Search .................................. 564/398, 434, 564/435, 397, 431, 432

[56] References Cited

U.S. PATENT DOCUMENTS

| | | | |
|---|---|---|---|
| 3,219,704 | 11/1965 | Wilder et al. | 260/576 |
| 4,431,841 | 2/1984 | Malz, Jr. et al. | 564/398 |
| 4,804,783 | 2/1989 | Nagata et al. | 564/402 |
| 4,952,731 | 8/1990 | Nagata et al. | 564/402 |
| 5,292,953 | 3/1994 | Langer et al. | 564/277 |
| 5,338,885 | 8/1994 | Immel et al. | 564/398 |

FOREIGN PATENT DOCUMENTS 57-058648 4/1982 Japan.
60-193949 10/1985 Japan.

*Primary Examiner*—Brian M. Burn
*Attorney, Agent, or Firm*—Burns, Doane, Swecker & Mathis

[57] ABSTRACT

A process for the preparation of 4-methoxy-2,2',6-trimethyldiphenylamine, which comprises heating and reacting 2,6-dimethylcyclohexanone and 2-methyl-4-methoxyaniline in the presence of a dehydrogenation catalyst while removing the resultant hydrogen and water from the reaction system.

4 Claims, No Drawings

PROCESS FOR THE PREPARATION OF 4-METHOXY-2,2',6'-TRIMETHYLDIPHENYLAMINE

BACKGROUND OF THE INVENTION

1. Field of the Invention

This invention relates to an improved industrial process for the preparation of 4-methoxy-2,2',6'-trimethyldiphenylamine useful as an intermediate for the production of a color-forming agent for heat-sensitive or pressure-sensitive recording papers.

2. Description of the Related Art

4-Methoxy-2,2',6'-trimethyldiphenylamine has heretofore been prepared by dehydrobromination and deacylation of an acetylation product of 2-methyl-4-methoxyaniline and 2,6-dimethylbromobenzene or of 1-bromo- 4-methoxy-2-methylbenzene and an acetylation product of 2,6-dimethylaniline.

These conventional processes are, however, accompanied by drawbacks such as complex reaction steps and a low reaction velocity. With a view toward overcoming such drawbacks, the present inventors previously proposed a process for the preparation of 4-methoxy-2,2',6'-trimethyldiphenylamine in which 2,6-dimethylphenol is used as a hydrogen acceptor. While forming 2,6-dimethylhexanone in the reaction system, 2,6-dimethylcyclohexanone is reacted with 2-methyl-4-methoxyaniline in the presence of a hydrogen transfer catalyst to prepare 4-methoxy-2,2',6'-trimethyldiphenylamine (Japanese Patent Laid-Open No. 193949/1985, U.S. Pat. No. 4,804,783). Although this process has simplified the reaction steps and improved the reaction velocity, the process cannot be considered as an industrially satisfactory process, because the process has a drawback such as poor selectivity to 4-methoxy-2,2',6'-trimethyldiphenylamine. Accordingly, there is still need for further improvement in the process.

SUMMARY OF THE INVENTION

With a view toward improving the method disclosed in U.S. Pat. No. 4,804,783 referred to above and thus establishing an industrially advantageous process, the present inventors have proceeded with an investigation.

As a result, it has been found that the target product can be obtained in a higher yield by removing the resultant hydrogen and water from the reaction system as much as possible.

The present invention therefore provides a process for the preparation of 4-methoxy-2,2',6'-trimethyldiphenylamine, which comprises heating and reacting 2,6-dimethylcyclohexanone and 2-methyl-4-methoxyaniline in the presence of a dehydrogenation catalyst while removing the resultant hydrogen and water from the reaction system.

According to the present invention, 4-methoxy-2,2',6'-trimethyldiphenylamine can be obtained at high selectivity in a high yield, which have not been attained by any prior art technique. The present invention, therefore, has a great significance.

DETAILED DESCRIPTION OF THE INVENTION AND PREFERRED EMBODIMENTS

In the course of the investigation, it has been found that due to the insufficient ability of 2,6-dimethylphenol as a hydrogen acceptor, a large amount of hydrogen formed as a result of the dehydrogenation remains in the reaction system and that a Schiff base, an intermediate product between 2,6-dimethylcyclohexanone and 2-methyl-4-methoxyaniline, is catalytically hydrogenated by the hydrogen, resulting in a reduction in the selectivity to 4-methoxy-2,2',6'-trimethyldiphenylamine. It has also been found that the hydrogen formed as a result of the dehydrogenation is also used for the catalytic hydrogenolysis of the amines, thereby causing a reduction in the selectivity to 4-methoxy-2,2',6'-trimethyldiphenylamine. It has also been discovered that the target product can be obtained in a higher yield by removing the resultant water from the reaction system as much as possible.

Based on these findings, the present inventors have conducted extensive research. As a result, it has been found that the target product can be obtained at high selectivity by reacting 2,6-dimethylcyclohexanone and 2-methyl-4-methoxyaniline in the presence of a dehydrogenation catalyst while removing the resultant hydrogen and water from the reaction system, leading to the completion of the present invention.

In the process according to the present invention, the sequence of two reactions proceeds in a single step. One is to prepare a Schiff base, an intermediate, by dehydration reaction between 2-methyl-4-methoxyaniline and 2,6-dimethylcyclohexanone in the presence of an acid catalyst; and the other is to catalytically dehydrogenate the resultant intermediate in the presence of a dehydrogenation catalyst to obtain a target product, 4-methoxy-2,2',6'-trimethyldiphenylamine, while removing from the reaction system resultant hydrogen together with water by-produced upon formation of the Schiff base.

2,6-Dimethylcyclohexanone used for the process of the present invention can be prepared easily by hydrogenating 2,6-dimethylphenol in the presence of a known hydrogenation catalyst.

2-Methyl-4-methoxyaniline used for the process of the present invention can be prepared easily by hydrogenating o-nitrotoluene under acidic conditions in methanol as a solvent in the presence of a known hydrogenation catalyst.

The molar ratio of 2,6-dimethylcyclohexanone to 2-methyl-4-methoxyaniline employed in the process of this invention may fall within a range of from 2:1 to 1:2, preferably 2:1 to 1:1, more preferably 1:1 to 1.5:1. At any molar ratios outside the above range, the selectivity tends to lower.

In general, a suitable hydroreduction catalyst is also suited for dehydrogenation. The hydroreduction catalyst is therefore employed in the process of the present invention. Specific examples of the catalyst include Raney nickel, reduced nickel or nickel-carrying catalysts, Raney cobalt, reduced cobalt or cobalt-carrying catalysts, Raney copper, reduced copper or copper-carrying catalysts, catalysts of noble metals of Group VIII of the periodic table or of the noble metals borne on carbon, alumina, barium carbonate or the like, rhenium catalysts such as rhenium-carbon, and copper-chromium oxide catalysts. Among these catalysts, palladium catalysts are preferred, with palladium-carrying catalysts such as palladium-carbon, palladium-alumina and palladium-magnesia being particularly preferred. The catalyst may ordinarily be used in an amount of 0.001 to 0.2 gram-atom, preferably 0.004 to 0.1 gram-atom in terms of metal atoms per gram-molecule of 2-methyl- 4-methoxyaniline.

In the process of the present invention, it is desired to add, as a cocatalyst, an organic amine compound, alkali metal compound and/or alkaline earth metal compound.

Exemplary organic amine compounds include diethylenetriamine, pentamethyldiethylenetriamine, tributylamine, diamylamine, triamylamine, tetraethylenepentamine, triethanolamine and aminoethyl ethanolamine. Among them, pentamethyldiethylenetriamine is preferred.

Illustrative of the alkali metal compound and alkaline earth metal compound include inorganic compounds such as hydroxides, carbonates and bicarbonates of alkali metals and alkaline earth metals. Specific examples include lithium hydroxide, sodium hydroxide, potassium hydroxide, calcium hydroxide, magnesium hydroxide, sodium carbonate, potassium carbonate and sodium bicarbonate. Among them, sodium hydroxide and potassium hydroxide are preferred.

These cocatalysts may be used either singly or in combination. The cocatalyst may be added to the reaction system independently from the above-exemplified dehydrogenation catalyst. Alternatively, it is also possible to use a catalyst prepared by having such a cocatalyst additionally carried from a solution thereof subsequent to preparation of a noble-metal-carrying catalyst.

The cocatalyst may be used in an amount of at least 2 wt. %, preferably 5–150 wt. % based on the catalyst metal. Amounts greater than the upper limit tend to lead to lower a reaction velocity. Amounts smaller than the lower limit, on the other hand, tend to result in a lower yield. Particularly, the above-exemplified bases are each observed to be effective in inhibiting the deammonium reaction of 2-methyl-4-methoxyaniline.

In the process of the present invention, 2-methyl- 4-methoxyaniline can be charged in a reaction vessel at once or dropwise. Preferred is the dropwise charge, which makes it possible to prepare 4-methoxy-2,2',6'-trimethyldiphenylamine at high selectivity in a high yield. In this case, it is advantageous from the viewpoint of yield and operability to conduct dropwise addition of 2-methyl-4-methoxyaniline in the form of a mixed liquid with 2,6-dimethylcyclohexanone.

The reaction temperature can be selected generally from a range of from 150° C. to 300° C., preferably 180° C. to 250° C. Temperatures lower than 150° C. tend to result in a reduced reaction velocity. Temperatures higher than 300° C., on the other hand, tend to result in lowered selectivity.

Although no particular limitation is imposed on the reaction pressure in the process of the present invention, the reaction pressure within a range of from atmospheric pressure to 4.0 kg/cm$^2$G is preferred. Reaction pressures greater than 4.0 kg/cm$^2$G tend to result in products with lowered selectivity. To elevate the pressure, it is possible to feed a gas inert to the reaction in the reaction system or to use the vapor pressures of the raw materials, product and/or solvent.

It is possible to use a solvent in the process of the present invention. No particular limitation is imposed on the solvent, but 2,6-dimethylphenol is particularly preferred. A solution of 2,6-dimethylcyclohexanone in 2,6-dimethylphenol can be prepared by converting a portion of the 2,6-dimethylphenol into 2,6-dimethylcyclohexanone and the resultant solution can be used as is in the present invention.

In the process of the present invention, it is essential to remove water, which is by-produced upon dehydration, from the reaction system. When the resultant water is removed from the reaction system by using a non-aqueous azeotropic dehydrating agent such as benzene or toluene, the dehydration velocity increases and further, the target product can be obtained in a high yield. It is therefore preferred to use a non-aqueous azeotropic dehydrating agent. To obtain the target product in a higher yield, the water content in the reaction system should be maintained at 1% or lower, preferably 0.3% or lower, most preferably at 0.1% or lower.

In the process of the present invention, the above advantages can still be brought about without using an acid as a catalyst for the dehydration reaction. The use of an acid catalyst is, however, preferred because it accelerates the dehydration velocity. Specific examples of the acid catalyst include inorganic acids such as hydrochloric acid, sulfuric acid, nitric acid and phosphoric acid; and organic acids such as acetic acid, phenylacetic acid, trifluoroacetic acid, propionic acid, butyric acid, octylic acid, lauric acid, formic acid, benzoic acid and nucleus-substituted derivatives thereof, phenylsulfonic acid and nucleus substituted derivatives thereof, oxalic acid, phthalic acids (o-, m-, p-), trimellitic acid and pyromellitic acid and no particular limitation is imposed thereon. Preferred are organic acids such as benzoic acid, octylic acid, trifluoroacetic acid, phthalic acid and pyromellitic acid. The acid catalyst may be used in an amount of 0.5–20 wt. %, preferably 1–10 wt. %, based on 4-methoxy-2-methylaniline.

4-Methoxy-2,2',6'-trimethyldiphenylamine so formed can be obtained by subjecting the reaction mixture to distillation, crystallization, extraction or the like. For example, after the completion of the reaction, the reaction mixture is filtered, whereby the solid catalyst is separated and collected. The catalyst so collected is reusable. The filtrate is concentrated to recover the solvent. The solvent is returned as is to the reaction system. 4-Methoxy-2,2',6'-trimethyldiphenylamine in the reaction vessel is purified and separated by distillation, crystallization or the like.

The present invention will hereinafter be described in detail by examples and comparative examples.

EXAMPLE 1

A 500 ml stainless steel reaction vessel equipped with a dehydration fractionating column, a reflux condenser, a separating tank and a pressure regulating valve was provided as a reactor.

The reactor is designed so that the vapor which is formed in the reaction vessel is allowed to flow through the fractionating column, caused to condense in the reflux condenser and charged in the separating tank, a portion of an upper layer of the separated liquid in the tank being returned to the reaction vessel. In an upper part of the separation tank, a pressure regulating valve is installed to keep the pressure in the reaction system constant.

Charged in the reaction vessel were 159.2 g of a solution of 49.2 g (0.39 mole) 2,6-dimethylcyclohexanone in 2,6-dimethylphenol, which solution had been obtained beforehand by hydrogenating 2,6-dimethylphenol, 3.0 g of benzoic acid, 2.1 g of 5% Pd/C (product of Japan N.E. Chemcat Corp.) and 20 g of toluene and in the separating tank whose internal capacity was 100 ml, toluene was charged up in an amount sufficient to reach a tube through which toluene was returned to the reaction vessel.

Nitrogen was charged to purge the gaseous phase in the reaction system and to change the internal pressure to 1.5 kg/cm$^2$G and then, the temperature was gradually raised. When the liquid temperature of the reaction vessel reached 150° C., the internal pressure became 2.0 kg/cm$_2$G. While keeping the internal pressure at 2.0 kg/cm$^2$G by using the pressure regulating valve, heating was continued until the temperature reached 220° C. At that time, the temperature of the top of the dehydration fractionating column reached 160° C. While maintaining the temperature and internal pressure under stirring, 41.2 g (0.3 mole) of 4-methoxy-2-methylaniline in the dropping funnel were charged dropwise into the reaction vessel over 5 hours. Water vapor, which started occurring concurrently with the initiation of the dropwise addition of 4-methoxy-2-methylaniline, began to distill out with toluene from the dehydration fractionating column. They were cooled in the reflux condenser, followed by separation into toluene and water in the separating tank. In the separating tank, water was isolated in the lower layer and toluene in the upper layer. A portion of the toluene in the upper layer was returned from the separating tank to the reaction vessel. Hydrogen which was emitted at the same time was continuously removed from the reaction system by using the pressure regulating valve so that the internal pressure was maintained at 2.0 kg/cm$^2$G. After the completion of the dropwise addition, stirring was continued for two hours while maintaining the temperature and the internal pressure. The contents of the reaction vessel were then cooled and 5% Pd/C was filtered off from the reaction mixture. As a result of an analysis of a portion of the filtrate by gas chromatography, it was found that the conversion rate of 4-methoxy-2-methylaniline was 95.1% and the selectivity to 4-methoxy-2,2',6'-trimethyldiphenylamine was 94.3%.

EXAMPLE 2

In a similar manner to Example 1, 110.0 g of 2,6-dimethylphenol, 0.75 g of isophthalic acid, 6.59 g of 5% Pd/C (water content: 50 wt. %; product of Japan N.E. Chemcat Corp.), a 1% solution of 1.65 g of pentamethyldiethylenetriamine in toluene and 20 g of toluene were charged in the reaction vessel. The temperature was raised to 225° C. and the internal pressure was kept at 1.0 kg/cm$^2$G. While maintaining the temperature and internal pressure under stirring, a mixed solution of 41.2 g (0.3 mole) of 4-methoxy-2-methylaniline and 49.2 g (0.39 mole) of 2,6-dimethylcylohexanone in a dropping funnel was added dropwise over 6 hours. In a similar manner to Example 1 except that the internal pressure was maintained at 1.0 kg/cm$^2$G and the reaction temperature was maintained at 225° C., the reaction was conducted and the reaction mixture was treated and analyzed. It was found that the conversion ratio of 4-methoxy- 2-methylaniline was 99.5% and the yield of 4-methoxy- 2,2',6'-trimethyldiphenylamine was 96 5% (selectivity: 97.0%).

Comparative Example 1

Using the reaction apparatus employed in Example 1, reactions and treatments were conducted in a similar manner to Example 1 except that resultant hydrogen and water vapor were not removed from the reaction system. The internal pressure of the reaction vessel rose from 2.3 kg/m$^2$G (at the time of initiation of dropwise addition of 4-methoxy-2-methylaniline) to 3.5 kg/cm2G because the pressure regulating valve was not actuated. As a result of an analysis as in Example 1, the conversion rate of 4-methoxy-2-methylaniline was 97.1% and the selectivity to 4-methoxy-2,2',6'-trimethyldiphenylamine was 64.1%.

What is claimed is:

1. In a process for the preparation of 4-methoxy-2,2'-6'-trimethyldiphenylamine by heating and reacting 2,6-dimethylcyclohexanone and 2-methyl4-methoxyaniline in the presence of a dehydrogenation catalyst, the improvement comprising dropwise addition of 2-methyl-4-methoxyaniline into the reaction system, while removing from the reaction system the resultant hydrogen and water.

2. A process according to claim 1, wherein the dehydrogenation catalyst comprises palladium.

3. A process according to claim 1, wherein the reaction is conducted under atmospheric pressure to 4.0 kg/cm$^2$ G.

4. A process according to claim 1, wherein both of 2,6-dimethylcyclohexanone and 2-methyl-4-methoxyaniline are dropwise added into the reaction system.

* * * * *